United States Patent
Haak et al.

(10) Patent No.: US 11,622,745 B2
(45) Date of Patent: Apr. 11, 2023

(54) TRANS-SEPTAL PUNCTURE GUIDANCE HEART REPAIR

(71) Applicants: KONINKLIJKE PHILIPS N.V., Eindhoven (NL); THE REGENTS OF THE UNIVERSITY OF COLORADO, Denver, CO (US)

(72) Inventors: Alexander Haak, Bothell, WA (US); Robert Quaife, Aurora, CO (US); John Dougher Carroll, Littleton, CO (US); Marco Verstege, Eindhoven (NL); Niels Nijhof, Utrecht (NL); Onno Wink, Seattle, WA (US)

(73) Assignees: KONINKLIJKE PHILIPS N.V., Eindhoven (NL); THE REGENTS OF THE UNIVERSITY OF COLORADO, Denver, CO (US)

( * ) Notice: Subject to any disclaimer, the term of this patent is extended or adjusted under 35 U.S.C. 154(b) by 75 days.

(21) Appl. No.: 16/967,779

(22) PCT Filed: Feb. 2, 2019

(86) PCT No.: PCT/EP2019/052556
§ 371 (c)(1),
(2) Date: Aug. 6, 2020

(87) PCT Pub. No.: WO2019/154737
PCT Pub. Date: Aug. 15, 2019

(65) Prior Publication Data
US 2021/0038186 A1    Feb. 11, 2021

Related U.S. Application Data

(60) Provisional application No. 62/626,896, filed on Feb. 6, 2018.

(51) Int. Cl.
*A61B 8/08*   (2006.01)
*A61B 8/00*   (2006.01)

(52) U.S. Cl.
CPC ............ *A61B 8/0883* (2013.01); *A61B 8/463* (2013.01); *A61B 8/466* (2013.01); *A61B 8/483* (2013.01); *A61B 8/5246* (2013.01); *A61B 8/54* (2013.01)

(58) Field of Classification Search
CPC ....... A61B 8/0883; A61B 8/463; A61B 8/466; A61B 8/483; A61B 8/5246; A61B 8/54;
(Continued)

(56) References Cited

U.S. PATENT DOCUMENTS

2009/0137952 A1* 5/2009 Ramamurthy ........... A61B 8/48
   604/95.01
2012/0296196 A1* 11/2012 Boese .................... A61B 6/503
   600/411

(Continued)

FOREIGN PATENT DOCUMENTS

WO    2006094222 A2    9/2006
WO    WO-2006094222 A2 *  9/2006  ............... A61B 5/06

OTHER PUBLICATIONS

PCT/EP2019/052556 ISR & WO, dated May 14, 2019, 13 Pages.

*Primary Examiner* — Joseph M Santos Rodriguez
*Assistant Examiner* — Kaitlyn E Sebastian

(57) ABSTRACT

A controller for displaying a puncture site of an intra-atrial septum for heart repairs includes a memory and a processor (710). The processor (710) executes instructions (784) to perform a process based on image data of a heart that includes a mitral valve and an intra-atrial septum. The process includes defining a mitral valve annulus plane along a mitral valve annulus of the mitral valve and a normal vector perpendicular to the mitral valve annulus plane. The process also includes defining an offset plane that intersects
(Continued)

with the intra-atrial septum and that is parallel to the mitral valve annulus plane. A safe zone for the puncture site is identified and displayed on the intra-atrial septum. The safe zone is between a lower boundary plane (456) and an upper boundary plane (455) that are each parallel to the offset plane by specified distances.

20 Claims, 10 Drawing Sheets

(58) Field of Classification Search
CPC ........... G06T 2210/41; G06T 2219/008; G06T 19/00
See application file for complete search history.

(56) References Cited

U.S. PATENT DOCUMENTS

| | | | |
|---|---|---|---|
| 2013/0038707 A1* | 2/2013 | Cunningham | A61B 1/0005 348/65 |
| 2015/0157459 A1 | 6/2015 | Macoviak et al. | |
| 2016/0030008 A1* | 2/2016 | Gerard | G06T 7/30 600/440 |
| 2017/0290570 A1* | 10/2017 | Yamamoto | A61B 8/463 |

* cited by examiner

TRANS-SEPTAL PUNCTURE GUIDANCE HEART REPAIR

CROSS-REFERENCE TO PRIOR APPLICATIONS

This application is the U.S. National Phase application under 35 U.S.C. § 371 of International Application No. PCT/EP2019/052556, filed on Feb. 2, 2019, which claims the benefit of U.S. Provisional Patent Application No. 62/626,896, filed on Feb. 6, 2018. These applications are hereby incorporated by reference herein.

BACKGROUND

The mitral valve is a valve in the heart that regulates blood flow between two functional components of the heart, i.e., from the left atrium to the left ventricle. FIG. 1A shows a simplified system representation of aspects of heart functionality to provide context. In FIG. 1A, blood flows through valves from a left atrium to a left ventricle and then on to the aorta, and also through valves from a right atrium to a right ventricle and then on to a pulmonary artery. The left atrium and the right atrium are partitioned by an intra-atrial septum. The simplified system representation in FIG. 1A does not reflect some aspects of an actual heart, such as that the elements therein are part of a living being and may expand, contract and move relative to one another on an ongoing basis, or also that the left atrium and right atrium are separated only by the intra-atrial septum and not open space. FIG. 1F illustrates a more realistic overhead view of portions of the heart illustrated in FIG. 1A, including the mitral valve MV visually enclosed within the left atrium LA when viewed from overhead, and the tricuspid valve TV visually enclosed within the right atrium RA when viewed from overhead.

FIG. 1B illustrates a side-view of the mitral valve on which a three-dimensional coordinate system is superimposed. In FIG. 1B, the axis 102 corresponds to the echo plane that shows the superior/inferior (head/foot) view of the LA and RA including the inferior vena cava (IVC) and superior vena cava (SVC). Axis 104 shows the anterior and posterior aspect of the heart in the context of a human body. The above-mentioned echo views are usually used during guidance of the trans-septal puncture. In a four-chamber view the height of the trans-septal puncture (TSP) position above the mitral valve is measured from or along the axis 106.

When the mitral valve is damaged, a TSP is an important task used in procedures for repairing or replacing the mitral valve. An example of the effects of mitral valve damage is mitral valve regurgitation, which is when blood that is supposed to flow only from the left atrium to the left ventricle leaks backwards through the mitral valve when the left ventricle contracts. Mitral valve regurgitation can be addressed, for example, by coapting (drawing together) separated tissue in the mitral valve leaflets and holding the leaflets together with a clip. TSP involves puncturing the intra-atrial septum and maneuvering to the damaged tissue of the mitral valve through the left atrium. The TSP may be sub-optimal if the intra-atrial septum is punctured too close or too far from the mitral valve, and this in turn can translate into difficulties in navigating and placing the clip. In the context of FIG. 1B, likelihood of complications when navigating the clip to the damaged tissue may increase with an increasing or decreased distance between the TSP and the axis 106.

FIG. 1C and FIG. 1D illustrate a known approach for TSP guidance using several two-dimensional (2D) real time views known respectively as the bicaval view and the perpendicular cross-sectional view. In FIG. 1C and FIG. 1D, the TSP is guided with these ultrasound views in two planes focusing on the intra-atrial septum, but not the mitral valve. The left atrium is designated LA, the right atrium is designated RA, the aorta is designated Ao, and the label for "tenting" shows where the intra-atrial septum is being pushed by the needle from the right atrium RA to the left atrium LA. In practice, during a procedure an interventionalist may switch to a 4-chamber view as in FIG. 1E to estimate the height of the TSP over the mitral valve coaptation plane indicated by the two-way arrows in FIG. 1E. The 4-chamber view in FIG. 1E is often used to relate the mitral valve to the TSP by measuring the height between the location where the leaflet tissue in the mitral valve is to be drawn together (the mitral valve coaptation) and the anticipated TSP position. The position of the clip is not necessarily at a damaged part of the tissue, as the clip can be placed at another location. Additionally, though reference herein may be to "damaged" tissue, it may be that the tissue is not damaged, such as when the valve does not close correctly due to surrounding tissue being too large.

However, depending on the anatomy, the 4-chamber view as in FIG. 1E and the bicaval view as in FIG. 1C may not always cut through the exact same locations on the intra-atrial septum. Additionally, even when the 4-chamber view as in FIG. 1E cuts through the mitral valve, the 4-chamber view only visualizes one point of the mitral valve coaptation plane. The angle between the 2D ultrasound plane as in FIG. 1E (4-chamber view) and the mitral valve coaptation plane may not be perpendicular, which can result in incorrectly large estimates of the TSP location relative to the mitral valve coaptation plane and lead to incorrect estimates of height.

Accordingly, a major problem when performing TSP for mitral valve repair is the disconnected visualization of the device landing zone in the mitral valve and the TSP location on the intra-atrial septum. Mitral valve repair usually requires a TSP with a specific height over the mitral valve coaptation plane and a specific angle relative to the axis spanned by the MV trigones, or at least a minimum height and at most a maximum height and/or at least a minimum angle relative to the axis spanned by the MV trigones. Due to the absence of the mitral valve in FIG. 1C and FIG. 1D, no relation to the actual landing zone on the mitral valve is established when viewing FIG. 1C and FIG. 1D. For measuring the height between the TSP and the mitral valve coaptation plane the different 4-chamber ultrasound view in FIG. 1E needs to be established, followed sometimes by another ultrasound view and typically by corrective maneuvers of the trans-septal catheter/needle. This process can be quite cumbersome, time consuming and un-intuitive.

As explained above, it is difficult to capture the 3D orientation and position of the mitral valve coaptation plane using only 2D ultrasound views. A preliminary study, conducted at the University of Colorado, compared 3D-based measurements to 2D ultrasound heights measured after catheter crossing of the intra-atrial septum via TSP. FIG. 1G illustrates the preliminary study results comparing heights from 2D ultrasound on the left and a 3D method on the right. The 2D heights were estimated in a 4-chamber view as in FIG. 1E. The 3D heights were estimated based on markers placed on the mitral valve coaptation plane within a 3D ultrasound volume. As can be seen, for the second and sixth subjects of the study, the differences between 2D and 3D height estimates were visually significant and during the procedure it was noted that the TSP was too low requiring corrective maneuvers. This may indicate deficiencies with the 2D ultrasound methods. That is, for patients 2 and 6 in FIG. 1G, insufficient height estimations from 2D ultrasound correlated to the two largest height difference with 3D measurements, suggesting a need for improvement in current TSP guidance methods using only 2D ultrasound views.

SUMMARY

According to a representative embodiment, a controller for displaying a puncture site of an intra-atrial septum for heart repairs includes a memory that stores instructions, and a processor that executes the instructions. When executed by the processor, the instructions cause the controller to execute a process. The process includes receiving image data of a heart. The heart includes a mitral valve and an intra-atrial septum, and the mitral valve includes a mitral valve annulus. The process also includes defining a modified mitral valve annulus plane parallel to the mitral valve annulus describing the plane of the leaflet defect as well as a normal vector perpendicular to the mitral valve annulus plane. The process further includes defining an offset plane that intersects with the intra-atrial septum. The offset plane is parallel to the mitral valve annulus plane and is located at a distance that is offset from the mitral valve annulus plane by an offset amount. Imagery of the heart is displayed based on the image data. The process also includes identifying and displaying a safe zone on the intra-atrial septum located above a lower boundary plane and below an upper boundary plane. The lower boundary plane is located parallel to the offset plane and is offset by a first specified distance below the offset plane and the upper boundary plane is located parallel to the offset plane and offset by a second specified distance above the offset plane.

According to another representative embodiment, a method for displaying an optimal puncture site of an intra-atrial septum for heart repairs includes receiving image data of a heart. The heart includes a malfunctioning part such as a mitral valve or another valve and bather such as an intra-atrial septum. An access point through the bather is to be identified to access the malfunctioning part. A measurable plane that can be measured passes through or along the measurable part and has a normal vector. The method includes identifying, by a processor that executes instructions stored in a memory, the measurable plane through or along the measurable part. The method also includes identifying an offset plane that intersects with the bather, wherein the offset plane is parallel to the measurable plane and is located at a distance that is offset from the measurable plane by a predetermined offset amount. Imagery of the heart is displayed on a display based on the image data. The method also includes displaying an optimal puncture site point (or zone) on the bather within a safe zone. The safe zone is an area on the bather located above a lower boundary plane and below an upper boundary plane. The lower boundary plane is located parallel to the offset plane and offset by a safe distance below the offset plane and the upper boundary plane is located parallel to the offset plane and offset by a safe distance above the offset plane.

According to another representative embodiment, a system for displaying a puncture site of an intra-atrial septum for heart repairs includes a controller, a medical imaging system, and a display. The controller includes a memory that stores instructions, and a processor that executes the instructions. The medical imaging system generates image data of a heart. The heart includes a mitral valve and an intra-atrial septum, and the mitral valve includes a mitral valve annulus. The display is controlled by the controller to display images of the heart based on the image data. When executed by the processor, the instructions cause the controller to execute a process including receiving the image data of the heart from the medical imaging system and defining a mitral valve annulus plane along the mitral valve annulus and a normal vector perpendicular to the mitral valve annulus plane. The process also includes defining an offset plane that intersects with the intra-atrial septum. The offset plane is parallel to the mitral valve annulus plane and is located at a distance that is offset from the mitral valve annulus plane by an offset amount. The images of the heart are displayed on the display. The process also includes identifying and displaying on the display a safe zone on the intra-atrial septum located above a lower boundary plane and below an upper boundary plane. The lower boundary plane is located parallel to the offset plane and is offset by a first specified distance below the offset plane and the upper boundary plane is located parallel to the offset plane and offset by a second specified distance above the offset plane.

BRIEF DESCRIPTION OF THE DRAWINGS

In the Summary above, in this Description, in the Claims below, and in the accompanying drawings, reference is made to particular features (including method steps) of trans-septal puncture guidance for mitral guide repair or replacement. It is to be understood that the present disclosure contemplates all possible combinations of such particular features. For example, where a particular feature is disclosed in the context of a particular aspect or embodiment, or a particular claim, that feature can also be used, to the extent possible, in combination with and/or in the context of other particular aspects and embodiments, and more generally in the invention(s) described herein.

The representative embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

Figure 1A:
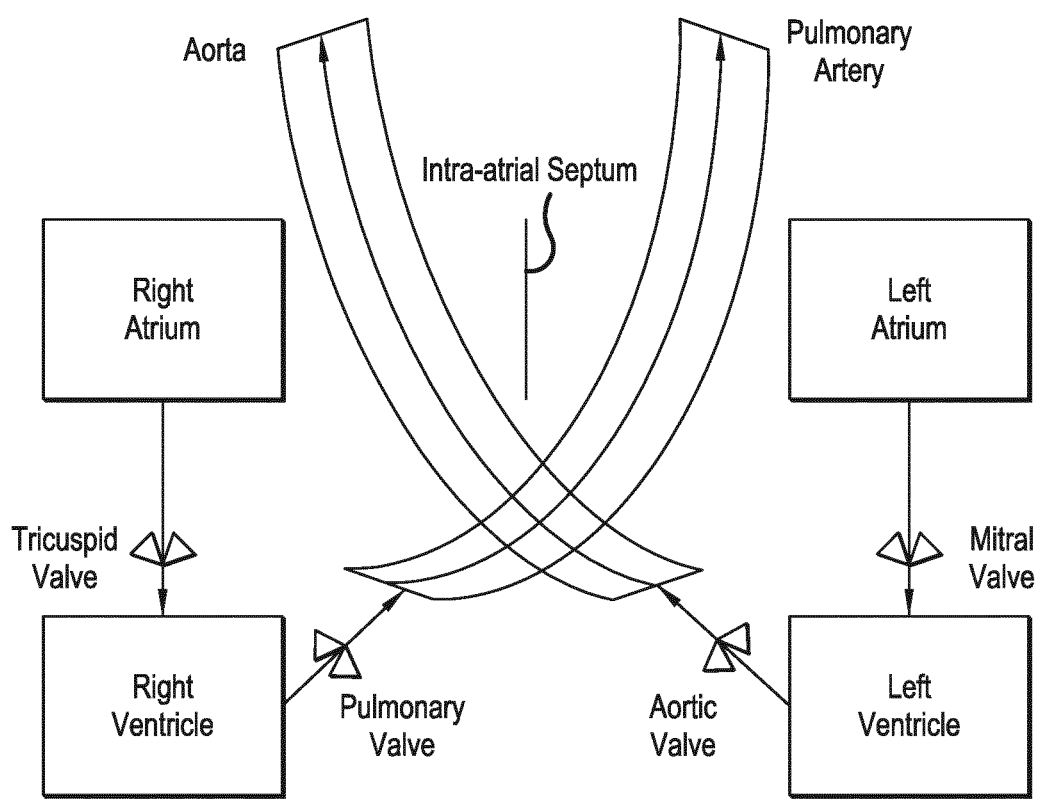
FIG. 1A illustrates a simplified system representation of known aspects of heart functionality to provide context for the descriptions herein.
Figure 1B:
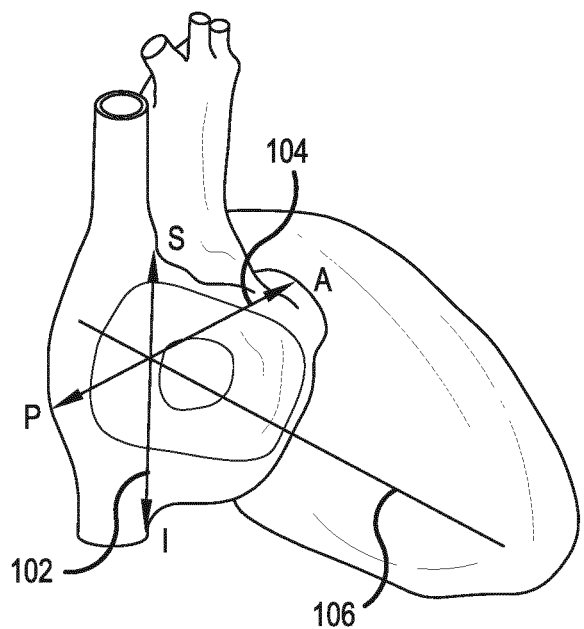
FIG. 1B illustrates a side-view of a mitral valve on which a three-dimensional coordinate system is superimposed.
Figure 1F:
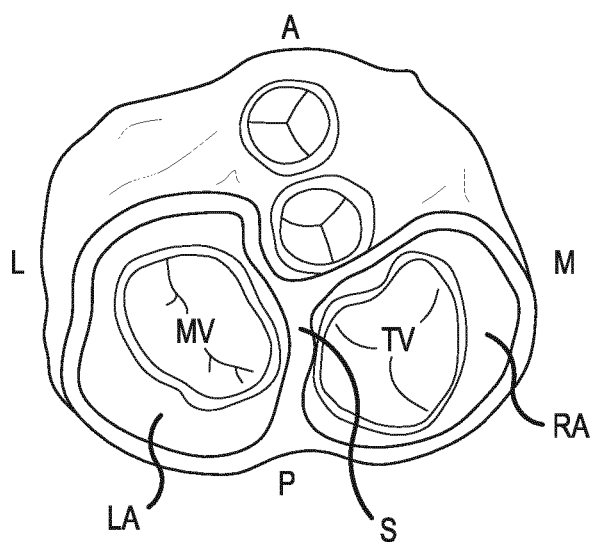
FIG. 1F illustrates a top view of a heart.
Figure 1C:
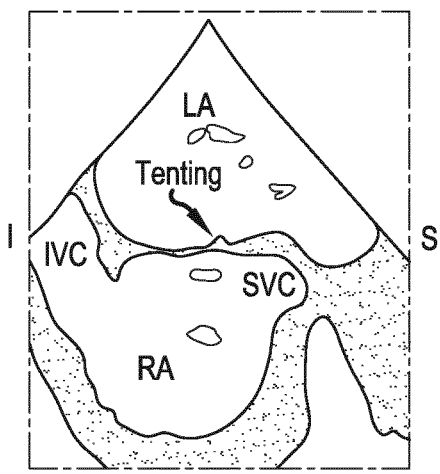
FIG. 1C illustrates a 2D bicaval ultrasound view in a known approach for TSP guidance.
Figure 1D:
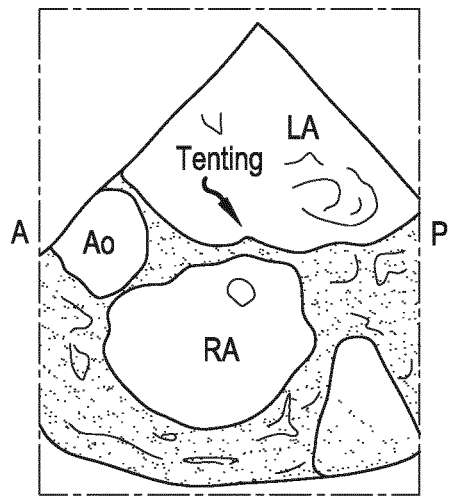
FIG. 1D illustrates a 2D perpendicular cross-sectional ultrasound view in the known approach for TSP guidance.
Figure 1E:
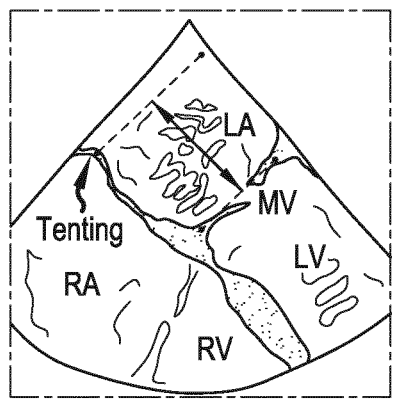
FIG. 1E illustrates a 4-chamber view used for estimating the height of the TSP over the mitral valve coaptation plane in the known approach for TSP guidance.
Figure 1G:
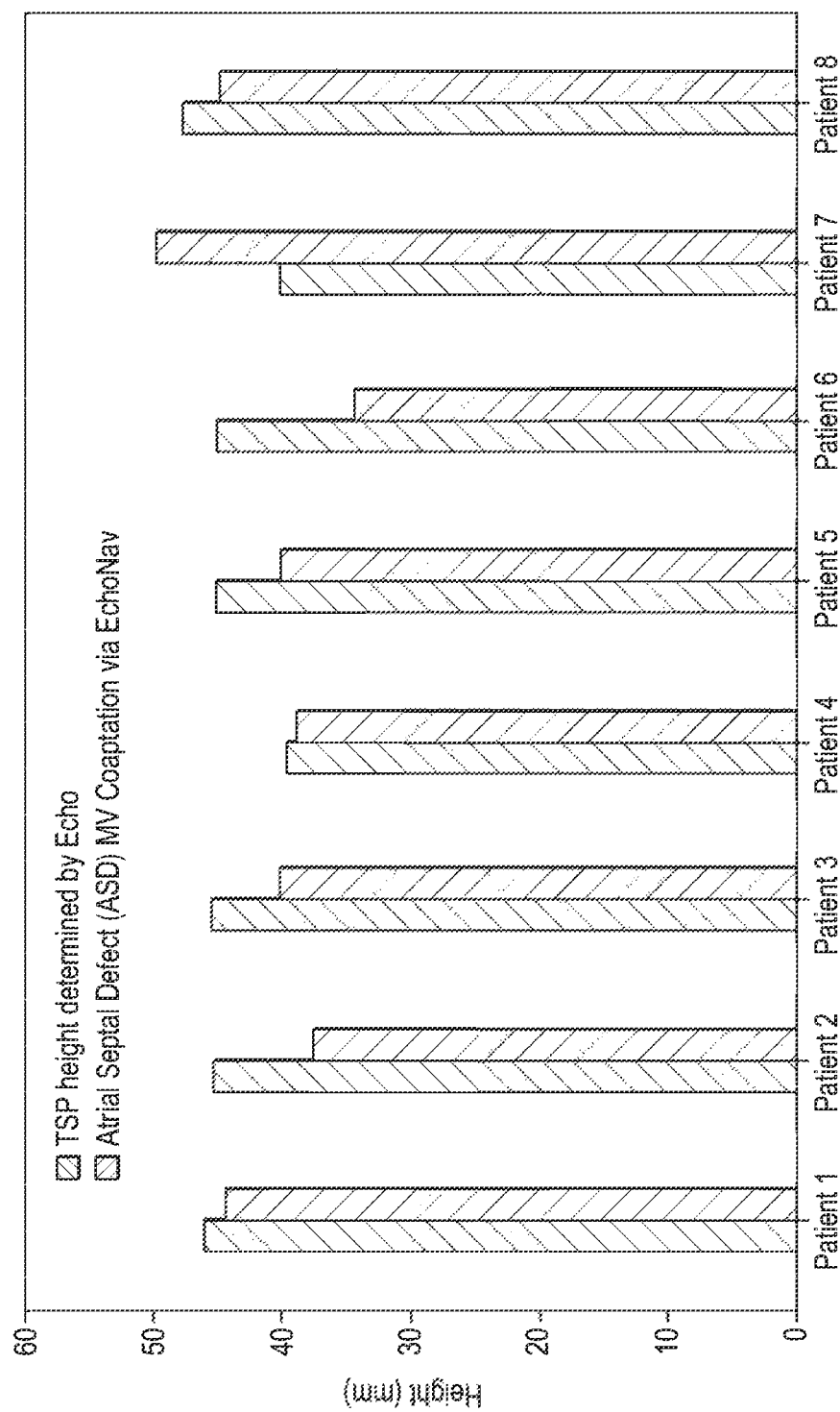
FIG. 1G illustrates a comparison of estimated heights of TSPs based on 2D ultrasound to measured heights of the same TSPs based on a 3D method.

Where reference is made herein to a method including two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm.

DETAILED DESCRIPTION

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only, and is not intended to be limiting. As used in the specification and appended claims, the singular forms of terms 'a', 'an' and 'the' are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In view of the foregoing, the present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

Figure 2:
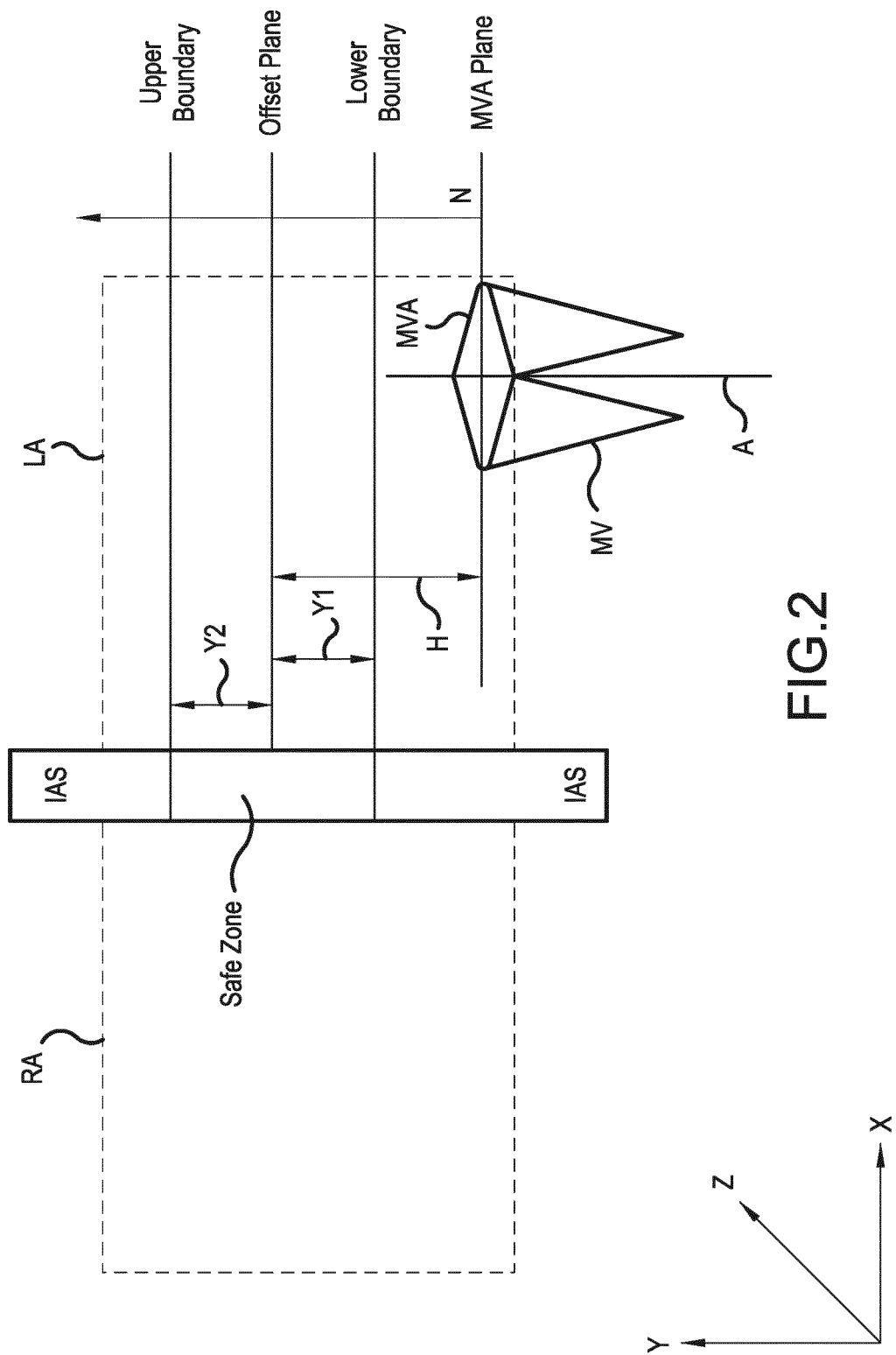
FIG. 2 illustrates a representation of the heart with geometric representations generated and displayed in trans-septal puncture guidance for heart repair, in accordance with a representative embodiment.

FIG. 2 illustrates a representation of the heart with geometric representations generated and displayed in trans-septal puncture guidance for heart repair, in accordance with a representative embodiment.

In FIG. 2, elements of a heart are represented by linear shapes that will almost always be different than the shapes of structures in any specific heart. Similarly, the relative sizes and spacing between elements of the heart in FIG. 2 are for ease of presentation to the viewer and reader and should not be considered representative of any specific heart in terms of sizes and spacing.

The relevant elements of the heart in FIG. 2 include the intra atrial septum IAS, the mitral valve MV including the mitral valve annulus MVA, along with the right atrium RA and the left atrium LA. A long axis A through the mitral valve MV represents the axis of the mitral valve through which blood flows from the left atrium to the left ventricle beneath. An MVA plane is based on three or more points identified on the surface of the mitral valve annulus, and a normal vector perpendicular to the MVA plane is delineated as N. An offset plane is parallel to the MVA plane and separated by a height H. A lower boundary plane is parallel to the offset plane and separated by the perpendicular distance Y1 therebetween. An upper boundary plane is parallel to the offset plane and separated by the perpendicular distance Y2 therebetween. A safe zone is identified on the intra-atrial septum IAS between the upper boundary and the lower boundary. An optimal puncture site may be identified within the safe zone by a point, circular area, or another area within the safe zone. The geometric representations in FIG. 2 will be referenced with respect to other FIGs. described below.

In FIG. 2, a 3D coordinate system is shown to include a width direction X, a height direction Y, and a depth direction Z. Insofar as trans-septal puncture guidance for heart repair may involve medical imaging systems such as ultrasound systems and X-ray systems, medical images may be assigned coordinates in 2D or 3D. The coordinate systems from different medical imaging systems described herein may be adjusted to one another in a process known as registration so that like locations in different image sets are assigned the same coordinates in a 3D coordinate system. As a result, references to features in geometric terms such as width, height and depth will be understood as implicitly reflecting a 3D coordinate system in common for any features described in such terms.

Embodiments of the present disclosure include generating and displaying imaging data related to the heart and specifically to the mitral valve and intra-atrial septum. This imaging data may be a 3D data set for visualizing the mitral valve and surrounding tissue, such as by 3D transesophageal echocardiogram (TEE). This data set may also be a polygon mesh describing the detail mitral valve apparatus with leaflets, annulus and leaflet coaptation. Preoperative computed tomography (CT) and magnetic resonance imaging (MRI) images may also be used to generate the models and zones described herein, and these too can in turn be registered and overlaid. A tool that can be used to perform such registration and overlaying is HeartNavigator from Philips of Eindhoven, Netherlands.

Figure 3:
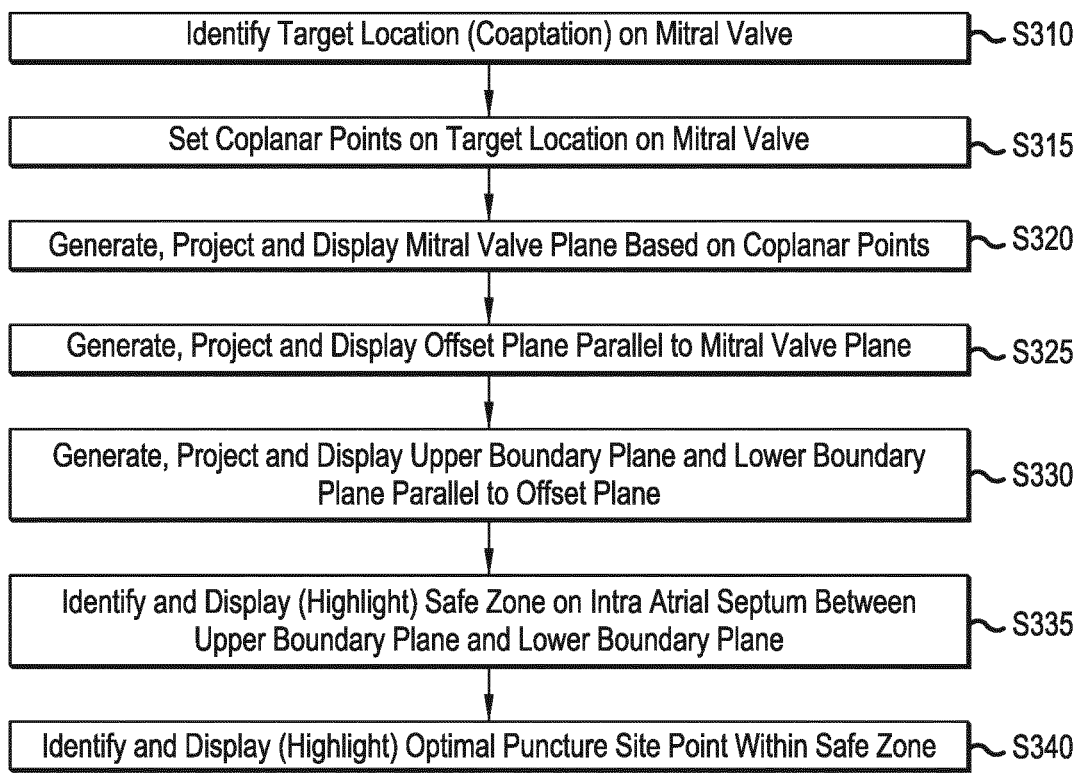
FIG. 3 illustrates a method for trans-septal puncture guidance for heart repair, in accordance with a representative embodiment.

FIG. 3 illustrates a method for trans-septal puncture guidance for heart repair, in accordance with a representative embodiment.

FIG. 3 describes a method for guiding a puncture through a barrier, and primarily references a trans-septal puncture through an intra-atrial septum. However, the bather is not restricted to an intra-atrial septum. Moreover, FIG. 3 describes the treatment location as a mitral valve. However, other malfunctioning parts of the heart can also be accessed and treated with teachings described herein. Accordingly, FIG. 3 more generally described a method for displaying an optimal puncture site of a bather such as an intra-atrial septum for heart repairs. The method includes receiving image data of a heart. The heart includes a malfunctioning part such as a mitral valve or another valve and the bather such as an intra-atrial septum. An access point through the bather is to be identified to access the malfunctioning part. A measurable plane that can be measured passes through or along the measurable part and has a normal vector. The method includes identifying, by a processor that executes instructions stored in a memory, the measurable plane through or along the measurable part. The method also includes identifying an offset plane that intersects with the barrier, wherein the offset plane is parallel to the measurable plane and is located at a distance that is offset from the measurable plane by a predetermined offset amount. Imagery of the heart is displayed on a display based on the image data. The method also includes displaying an optimal puncture site point (or zone) on the bather within a safe zone. The safe zone is an area on the bather located above a lower boundary plane and below an upper boundary plane. The lower boundary plane is located parallel to the offset plane and offset by a safe distance below the offset plane and the upper boundary plane is located parallel to the offset plane and offset by a safe distance above the offset plane.

In FIG. 3, the process starts at S310 by identifying a target location on a cardiac structure of interest such as the mitral valve. The target location may be a location of coaptation. The location of coaptation for a mitral valve may be the location to be treated, such as with a clip, and may be a tissue location on the mitral valve annulus for example. In a medical intervention involving a heart as described herein, measurements below or above the mitral valve annulus may be obtained depending on the leaflet defect being measured.

At S315, coplanar points on the target location on the mitral valve are set. For example, the coplanar points may be set and confirmed by a user visually inspecting an image based on image data returned from a first medical imaging system 610 and/or a second medical imaging system 640 described below with respect to FIG. 6. Alternatively, coplanar points may be set by automated image analysis performed by an image analysis computer 620 and/or base station 630 described below with respect to FIG. 6.

At S320, the process in FIG. 3 includes generating, projecting and displaying a mitral valve plane based on the coplanar points identified at S315. For example, the mitral valve plane may be generated in a three-dimensional coordinate system that includes the heart which includes the mitral valve. The mitral valve plane may be projected to identify intersections with other geometric area of interest, such as the intra-atrial septum IAS and the left atrium LA in FIG. 2. When the malfunctioning part is a part of the heart other than the mitral valve, the plane that is generated, projected and displayed corresponds to the malfunctioning part based on coplanar points on the target location of the malfunctioning part. As should be clear, the mitral valve is an example of a malfunctioning part, but points on another part such as a different valve can be measured and used to identify a measurable plane through or along the malfunctioning part. Accordingly, though FIG. 3 specifies that the malfunctioning part is a mitral valve, the features of FIG. 3 are equally applicable to other parts of the heart that malfunction on occasion, such as other valves.

At S325, the process in FIG. 3 includes generating, projecting and displaying an offset plane parallel to the mitral valve plane. The offset for the offset plane may be based on a predetermined offset distance that applies to all subjects of the trans-septal puncture guidance for heart repair. Alternatively, the offset for the offset plane may be dynamically based on a per-patient basis, so that the offset is determined only based on analysis of the physiology of any particular patient such as based on the condition of a patient's heart including the intra-atrial septum IAS and mitral valve MV. The offset may also be dynamically generated based on demographic characteristics of a patient such as age, gender, height, weight etc. The offset may also be dynamically generated based on the selected devices used for the intervention. The selected devices may correlate with characteristics of the anatomy but may also be selected based on other factors such as availability, reimbursement and physician preference.

At S330, the method in FIG. 3 includes generating, projecting and displaying an upper boundary plane and a lower boundary plane parallel to the offset plane. The upper boundary plane and the lower boundary plane may be offset from the offset plane by distances that are predetermined or that are dynamically determined. Additionally, such offset distances may be the same or may be different. The offset distances may be the same when the offset plane is to be exactly between the upper boundary plane and the lower boundary plane.

At S335, the process in FIG. 3 includes identifying and displaying a safe zone on the intra atrial septum between the upper boundary plane and the lower boundary plane. The safe zone may be projected as an area between the upper boundary plane and the lower boundary plane that is projected onto the intra atrial septum. The display of the safe zone on a display device may be highlighted such as by color and/or brightness. The safe zone is therefore identified and displayed based on a first specified distance and a second specified distance from the offset plane, and the first specified distance and the second specified distance define levels between which puncture of the intra-atrial septum is determined to be safe or relatively safe compared to other areas of the intra-atrial septum.

At S340, the process in FIG. 3 includes identifying and displaying an optimal puncture site within the safe zone. The display of the optimal puncture site on a display device may be highlighted such as by color and/or brightness, and may be a single point, a smaller area than the safe zone, a different shape than the safe zone, a different color and/or brightness than the safe zone, or other ways to highlight the optimal puncture site within the safe zone.

In one or more embodiments that include some or all of the features described for FIG. 3, a method for displaying an optimal puncture site of an intra-atrial septum for heart repairs may include receiving image data of a heart. The heart includes a mitral valve and an intra-atrial septum, and the mitral valve includes a mitral valve annulus. The method in these embodiments may include identifying a mitral valve annulus plane along the mitral valve annulus by identifying three or more coplanar points on the annulus. The mitral valve annulus plane has a normal vector. An offset plane may be identified. The offset plane is parallel to the mitral valve annulus plane and is located at a distance that is offset from the mitral valve annulus plane by a predetermined offset amount. The offset plane intersects with the intra-atrial septum. Image data of the heart may be displayed along with an optimal puncture site point on the intra-atrial septum within a safe zone. The safe zone is an area on the intra-atrial septum located above a lower boundary plane and below an upper boundary plane. The lower boundary plane is located parallel to the offset plane and offset by a safe distance below the offset plane and the upper boundary plane is located parallel to the offset plane and offset by a safe distance above the offset plane.

In a subset of the one or more embodiments described immediately above, a method may include identifying an axis 102 of the mitral valve. The long axis 102 has an axial direction. A long axis plane that passes through the axis 102 and is parallel to the normal vector may be identified. The long axis plane intersects with the offset plane. The optimal puncture site point on the intra-atrial septum may be identified and displayed at the intersection of the long axis plane and the offset plane.

In an example, an ultrasound or other imaging mode may be used to obtain live image data of the heart that is captured live during a medical intervention, such as using a second medical imaging system 640 described later with respect to FIG. 6. Previous three-dimensional image data of the heart may have been captured previously, such as using a first medical imaging system 610 described later with respect to FIG. 6. A process executed, such as by a base station 630 or an image analysis computer 620 described later with respect to FIG. 6 may include co-registering live image data of the heart that is captured live during a medical intervention with previous three-dimensional image data of the heart that is captured previously, to generate the image data. In other embodiments, both sets of the image data that are co-registered may be live image data, such as three-dimensional image data captured by ultrasound imaging and X-ray imaging in a common setting.

Interventions described herein consistently reference a "clip" as the tool to be used to treat a malfunctioning mitral valve. However, the teachings described herein are not limited to clips, mitral valves, or even TSP necessarily. For example, navigation of other types of tools through a septum or similar barrier can be performed based on the teachings described herein. As an example, a so-called annuloplasty device such as Cardioband™ is another type of tool that can be navigated through a barrier at a location optimized based on the teachings described herein, and an annuloplasty device is only another example of devices that can be navigated. The teachings herein extend to other types of devices and tools navigated for placement in interventions. Additionally, the intended purpose of the tool that is navigated through a bather using the teachings herein is not limited to tools for valve repair. In embodiments, tools for valve replacement may also be the tools that are navigated through a bather using the teachings herein.

Figure 4A:
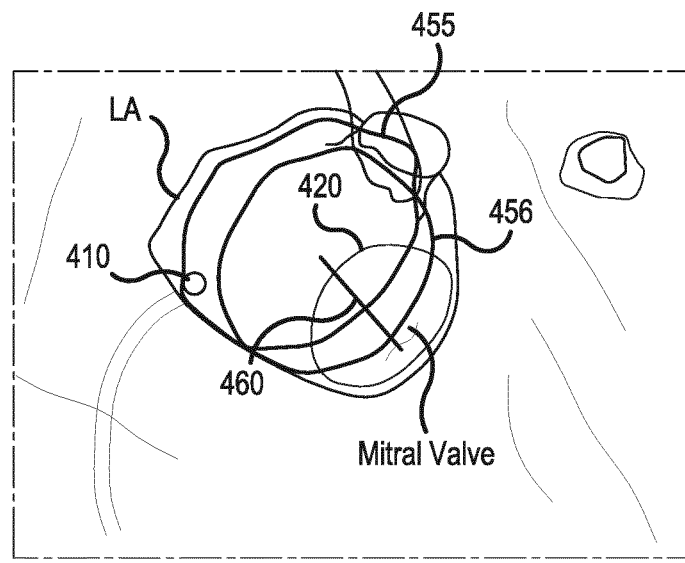
FIG. 4A illustrates a projected view of a left atrium and mitral valve with geometric representations generated and displayed in trans-septal puncture guidance for heart repair superimposed therein, in accordance with a representative embodiment.

FIG. 4A illustrates a projected view of a left atrium and mitral valve with geometric representations generated and displayed in trans-septal puncture guidance for heart repair superimposed therein, in accordance with a representative embodiment.

In FIG. 4A, the TSP location 410 is defined based on the mitral valve coaptation plane 420. The mitral valve coaptation plane 420 may be translated by a predefined distance (e.g. ~4 cm) into the left/right atria and the TSP location 410 may be indicated by a point displayed onto the intra-atrial septum. Moreover, the optimal TSP height may be indicated by linearly projecting (e.g., with a projection line 460) two planar rings onto the intra-atrial septum representing the lower boundary plane 456 and upper boundary plane 455 of an optimal TSP. Additionally, a heat map indicating an acceptable height and MV commissural axis 461 may be displayed. FIG. 4A shows such a left atrial mesh labelled as LA, a mitral valve mesh labelled as Mitral Valve and the puncture zone between the lower boundary plane 456 and the upper boundary plane 455 projected onto a live fluoroscopy screen.

Figure 4B:
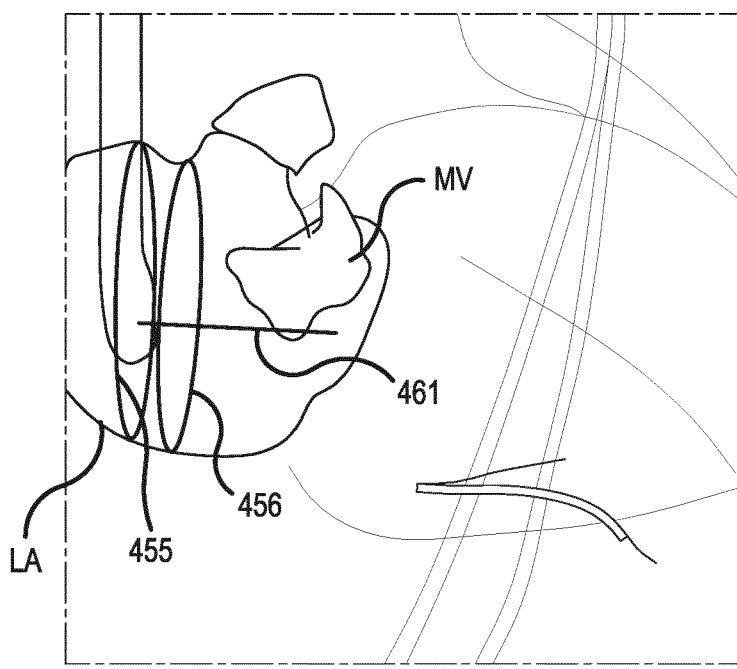
FIG. 4B illustrates a side view of a left atrium and mitral valve with geometric representations generated and displayed in trans-septal puncture guidance for heart repair superimposed therein, in accordance with a representative embodiment.

FIG. 4B illustrates a side view of a left atrium and mitral valve with geometric representations generated and displayed in trans-septal puncture guidance for heart repair superimposed therein, in accordance with a representative embodiment.

In FIG. 4B, an optimal puncture zone is defined between the lower boundary plane 456 and the upper boundary plane 455. The MV commissural axis 461 is shown projecting from the mitral valve coaptation plane in the direction of the lower boundary plane 456 and the upper boundary plane 455. The safe zone may be an optimal puncture zone projected onto a left atrial polygon mesh for the intra-atrial septum. FIG. 4B shows the puncture zones between the lower boundary plane 456 and the upper boundary plane 455 at an x-ray projection almost perpendicular to the mitral valve plane.

Figure 4C:
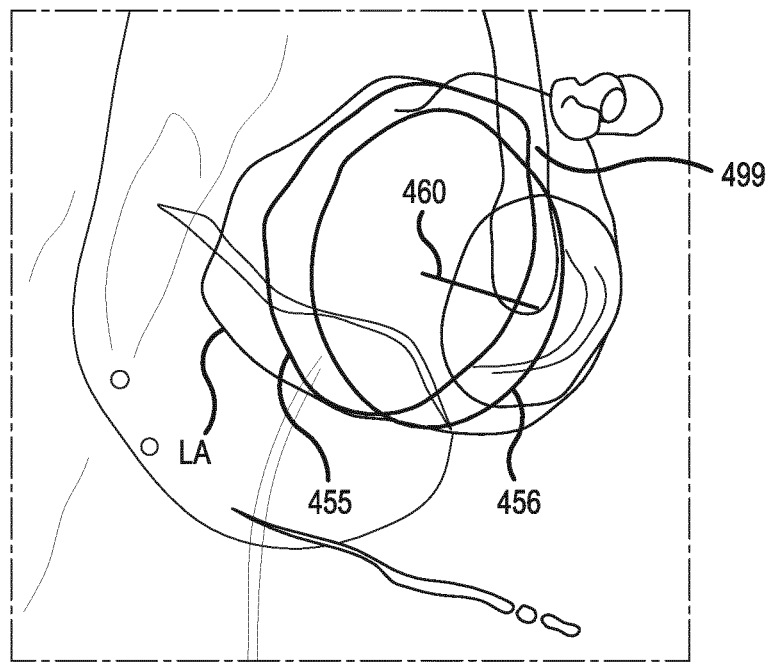
FIG. 4C illustrates another projected view of a left atrium and mitral valve with geometric representations generated and displayed in trans-septal puncture guidance for heart repair superimposed therein, in accordance with a representative embodiment.

FIG. 4C illustrates another projected view of a left atrium and mitral valve with geometric representations generated and displayed in trans-septal puncture guidance for heart repair superimposed therein, in accordance with a representative embodiment.

In FIG. 4C, a septal puncture needle 499 is shown engaging between the lower boundary plane 456 and the upper boundary plane 455.

Figure 5:
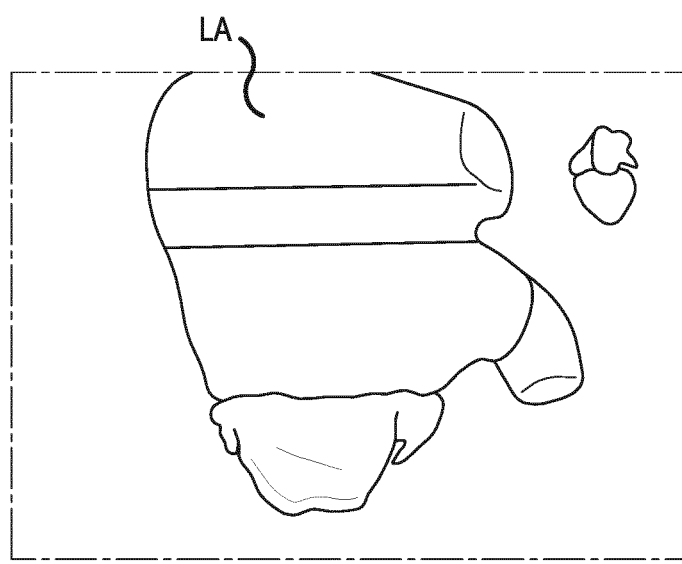
FIG. 5 illustrates a side view of a left atrium with an optimal puncture position displayed within a safe zone delineated by an upper boundary plane and a lower boundary plane generated and displayed in trans-septal puncture guidance for heart repair, in accordance with a representative embodiment.

FIG. 5 illustrates a side view of a left atrium with an optimal puncture position displayed within a safe zone delineated by an upper boundary plane and a lower boundary plane generated and displayed in trans-septal puncture guidance for heart repair, in accordance with a representative embodiment.

In FIG. 5, two lines on the left atrium model indicate an optimal puncture zone. The optimal puncture zone may be a safe zone identified using an investigational device such as the EchoNavigator from Philips of Eindhoven, Netherlands.

Figure 6:
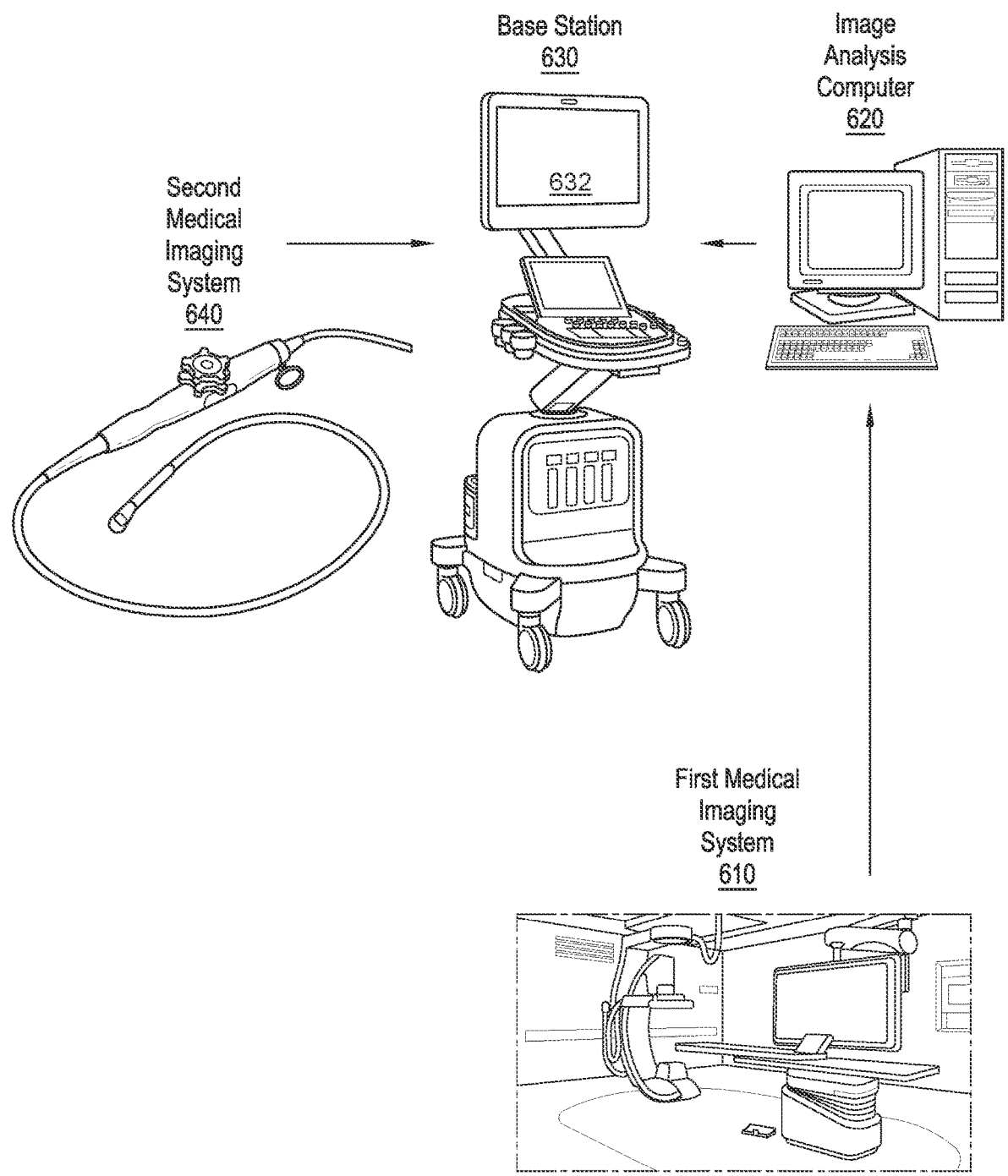
FIG. 6 illustrates a system for trans-septal puncture guidance for heart repair, in accordance with a representative embodiment.

FIG. 6 illustrates a system for trans-septal puncture guidance for heart repair, in accordance with a representative embodiment.

The system in FIG. 6 may be used for interventions to repair a mitral valve. However, other malfunctioning parts of a heart may also be repaired with teachings described herein. Additionally, approaches to the mitral valve or another malfunctioning part are not constricted to TSP, as different access points can be optimized based on measurements of the mitral valve or another malfunctioning part when the height from the access point to the mitral valve or another malfunctioning part is relevant. In other embodiments, the tricuspid valve or another heart valve is the malfunctioning part repaired based on teachings described herein relating to an approach with the same or similar height requirements.

In FIG. 6, the system for trans-septal puncture guidance for heart repair includes a first medical imaging system 610, an image analysis computer 620, a base station 630, and a second medical imaging system 640. An example of the first medical imaging system 610 is an X-ray system that includes an X-ray machine that performs fluoroscopy imaging. An example of the second medical imaging system 640 is a TEE Doppler ultrasound apparatus used to obtain transesophageal echocardiography (TEE) Doppler ultrasound imagery.

In FIG. 6, the imaging that results in the image data of the heart may be performed in real-time using the second medical imaging system 640 alone or using both the second medical imaging system 640 and the first medical imaging system 610. The second medical imaging system 640 provides image data to the base station 630, and processing by the base station 630 and/or the image analysis computer 620 results in functionality described herein.

In FIG. 6, the base station 630 includes a display 632. The display may be used to display imagery of the heart and the various geometric features described herein for trans-septal puncture guidance for heart repair. As the term "display" is used herein, the term should be interpreted to include a class of features such as a "display device" or "display unit". As any of the terms "display", "display device" or "display unit" are used herein, these terms encompass an output device, or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

As explained later with respect to FIG. 7, any of the elements in FIG. 6 may include a controller with a combination of a memory that stores instructions and a processor that executes the instructions in order to implement processes described herein. In an embodiment, such a controller may be implemented by the base station 630. The term "controller" broadly encompasses all structural configurations, as understood in the art of the present disclosure and as exemplary described in the present disclosure, of an application specific main board or an application specific integrated circuit for controlling an application of various inventive principles of the present disclosure as subsequently described in the present disclosure. The structural configuration of the controller may include, but is not limited to, processor(s), computer-usable/computer readable storage medium(s), an operating system, application module(s), peripheral device controller(s), slot(s) and port(s). A controller may be housed within or linked to a workstation. Examples of a "workstation" include, but are not limited to, an assembly of one or more computing devices, a display/monitor, and one or more input devices (e.g., a keyboard, joysticks and mouse) in the form of a standalone computing system, a client computer of a server system, a desktop or a tablet. Additionally, the descriptive labels for the term "controller" herein facilitate a distinction between controllers as described and claimed herein without specifying or implying any additional limitation to the term "controller".

Additionally, although FIG. 6 shows components networked together, two such components may be integrated into a single system. For example, the image analysis computer 120 may be integrated with the first medical imaging system 610 or with the base station 630. That is, in embodiments functionality attributed to the image analysis computer 620 may be implemented by (e.g., performed by) a system that includes the first medical imaging system 610 or a system that includes the base station 630. On the other hand, the four networked components shown in FIG. 6 may also be spatially distributed such as by being distributed in different rooms or different buildings, in which case the four networked components may be connected via data connections. In still another embodiment, one or more of the four components in FIG. 6 is not connected to the other components via a data connection, and instead is provided with input or output manually such as by a memory stick or other form of memory. In yet another embodiment, functionality described herein may be performed based on functionality of the elements in FIG. 6 but outside of the system shown in FIG. 6.

Any of the first medical imaging system 610, the image analysis computer 620, the base station 630, and the second medical imaging system 640 in FIG. 6 may include some or all elements and functionality of the general computer system described below with respect to FIG. 7. For example, the base station 630 may include a controller for displaying a puncture site of an intra-atrial septum for heart repairs, and the controller may include a memory that stores instructions and processor that executes the instructions. Alternatively, the image analysis computer 620 may include a controller for displaying a puncture site of an intra-atrial septum for heart repairs, and the controller may include a memory that stores instructions and processor that executes the instructions.

In either example above, when executed by the processor, the instructions cause the controller to execute a process, and the process may include receiving image data of a heart, wherein the heart includes a mitral valve and an intra-atrial septum, and the mitral valve includes a mitral valve annulus. Of course, in addition to or as an alternative to receiving the image data, the processor in a controller implemented by the base station 630 and/or the image analysis computer 620 may generate image data, such as based on signals received from the second medical imaging system 640 and/or signals received from the first medical imaging system 610.

The process implemented when a controller of the base station 630 and/or image analysis computer 620 executes instructions also includes defining a mitral valve annulus plane along the mitral valve annulus and a normal vector perpendicular to the mitral valve annulus plane. A mitral valve annulus is a fibrous ring that is attached to mitral valve leaflets and serves as an insertion site for the leaflet tissue. The mitral valve annulus may be considered the anatomical junction between the left atrium on top and the ventricle below. In FIG. 2, the mitral valve annulus was designated by MVA and is provided below most of the left atrium LA. The mitral valve annulus plane is along the mitral valve annulus. For example, the mitral valve annulus plane may be defined based on three or more points on the mitral valve annulus identified in an image of the mitral valve annulus. In FIG. 2, the normal vector is shown as the arrow pointing up and designated N, perpendicular to the mitral valve annulus plane.

The process implemented when a controller of the base station 630 and/or image analysis computer 620 executes instructions also includes defining an offset plane that intersects with the intra-atrial septum, wherein the offset plane is parallel to the mitral valve annulus plane and is located at a distance that is offset from the mitral valve annulus plane by an offset amount. In FIG. 2, the offset plane is shown above the mitral valve annuls plane by the height H.

The process implemented when a controller of the base station 630 and/or image analysis computer 620 executes instructions also includes displaying imagery of the heart based on the image data. In FIG. 2, the heart itself may be fully represented and included at least the intra-atrial septum designated IAS, the mitral valve MV including the mitral valve annulus MVA, the right atrium RA and the left atrium RA.

The process implemented when a controller of the base station 630 or image analysis computer 620 executes instructions moreover includes identifying and displaying a safe zone on the intra-atrial septum located above a lower boundary plane and below an upper boundary plane. The lower boundary plane is located parallel to the offset plane and is offset by a first specified distance below the offset plane and the upper boundary plane is located parallel to the offset plane and offset by a second specified distance above the offset plane. In FIG. 2, the safe zone is designated in the intra-atrial septum IAS and is defined by the upper boundary above the offset plane by the specified amount Y2 and the lower boundary below the offset plane by the specified amount Y1. Additionally, a long axis of the mitral valve MV is designated A and serves as an axis for the mitral valve MV in the direction of flow from the left atrium to the left ventricle beneath.

In one or more embodiments using one or more features in FIG. 6, a controller displays an optimal puncture site of an intra-atrial septum for heart repairs. The controller includes a memory that stores instructions, and a processor that executes the instructions. When executed by the processor, the instructions cause the controller to execute a process that includes receiving image data of a heart. The heart includes a mitral valve and an intra-atrial septum, and the mitral valve includes a mitral valve annulus. The process executed when the processor executes instructions may also include defining a mitral valve annulus plane along the mitral valve annulus. The mitral valve annulus plane has a normal vector. An offset plane may be defined. The offset plane is parallel to the mitral valve annulus plane and is located at a distance that is offset from the mitral valve annulus plane by a predetermined offset amount. The offset plane intersects with the intra-atrial septum. Image data of the heart may be displayed along with an optimal puncture site point on the intra-atrial septum within a safe zone. The safe zone is an area on the intra-atrial septum located above a lower boundary plane and below an upper boundary plane. The lower boundary plane is located parallel to the offset plane and offset by a safe distance below the offset plane and the upper boundary plane is located parallel to the offset plane and offset by a safe distance above the offset plane.

According to another subset of the embodiments described above, when executed by the processor, the instructions additionally cause the controller to execute a process that includes identifying an axis 102 of the mitral valve. The long axis 102 has an axial direction. A long axis plane that passes through the axis 102 and is parallel to the normal vector is also identified. The long axis plane intersects with the offset plane. The optimal puncture site point is displayed on the intra-atrial septum at the intersection of the axis 102 plane and the offset plane.

Figure 7:
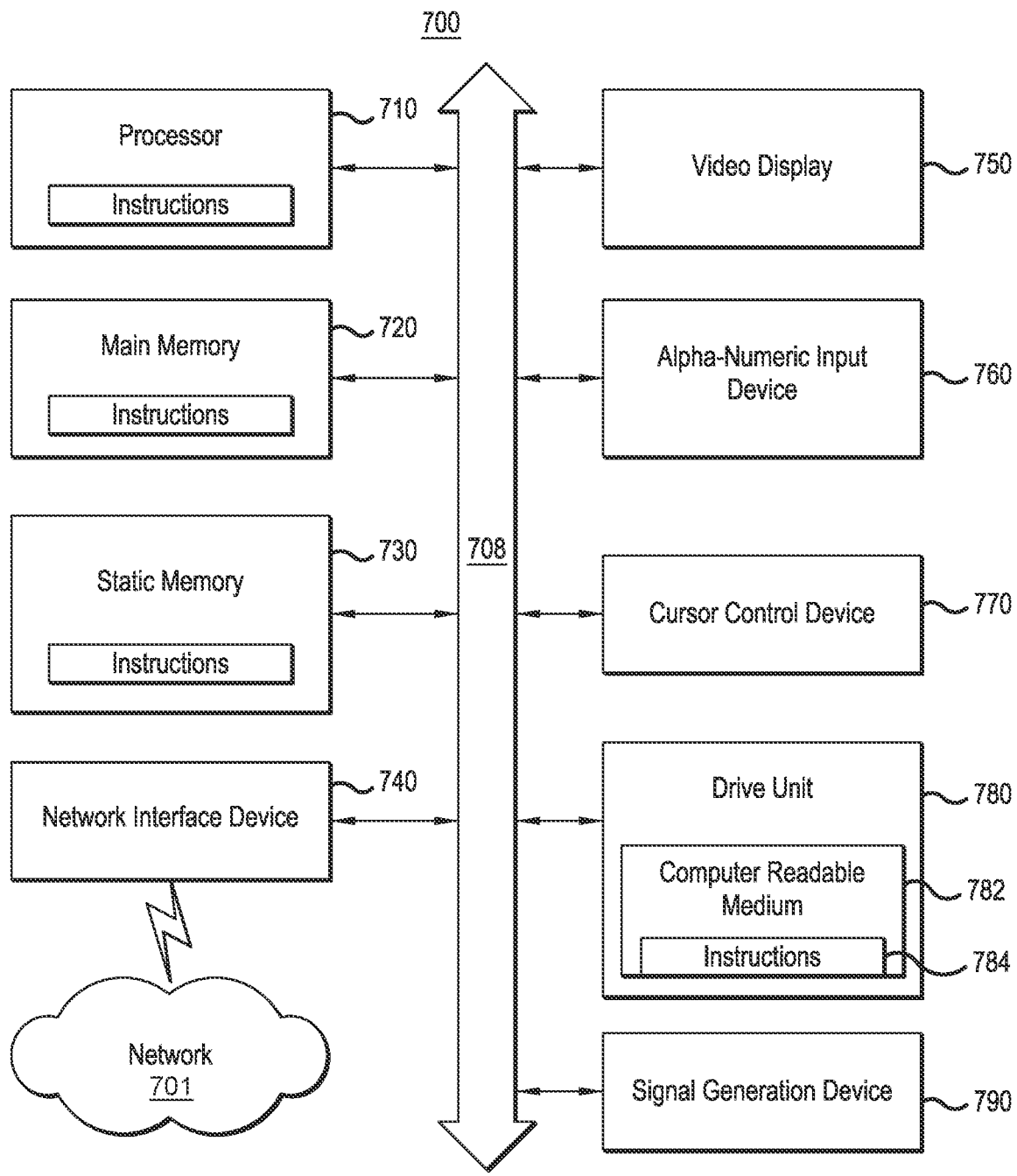
FIG. 7 illustrates a general computer system, on which a method of trans-septal puncture guidance for heart repair can be implemented, in accordance with another representative embodiment.

FIG. 7 illustrates a general computer system, on which a method of trans-septal puncture guidance for heart repair can be implemented, in accordance with another representative embodiment.

The computer system 700 can include a set of instructions that can be executed to cause the computer system 700 to perform any one or more of the methods or computer-based functions disclosed herein. The computer system 700 may operate as a standalone device or may be connected, for example, using a network 701, to other computer systems or peripheral devices.

In a networked deployment, the computer system 700 may operate in the capacity of a server or as a client user computer in a server-client user network environment, or as a peer computer system in a peer-to-peer (or distributed) network environment. The computer system 700 can also be implemented as or incorporated into various devices, such as the first medical imaging system 610, the image analysis computer 620, the base station 630, the second medical imaging system 640, a stationary computer, a mobile computer, a personal computer (PC), a laptop computer, a tablet computer, or any other machine capable of executing a set of instructions (sequential or otherwise) that specify actions to be taken by that machine. The computer system 700 can be incorporated as or in a device that in turn is in an integrated system that includes additional devices. In an embodiment, the computer system 700 can be implemented using electronic devices that provide voice, video or data communication. Further, while the computer system 700 is illustrated in the singular, the term "system" shall also be taken to include any collection of systems or sub-systems that individually or jointly execute a set, or multiple sets, of instructions to perform one or more computer functions.

As illustrated in FIG. 7, the computer system 700 includes a processor 710. A processor for a computer system 700 is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A processor is an article of manufacture and/or a machine component. A processor for a computer system 700 is configured to execute software instructions to perform functions as described in the various embodiments herein. A processor for a computer system 700 may be a general-purpose processor or may be part of an application specific integrated circuit (ASIC). A processor for a computer system 700 may also be a microprocessor, a microcomputer, a processor chip, a controller, a microcontroller, a digital signal processor (DSP), a state machine, or a programmable logic device. A processor for a computer system 700 may also be a logical circuit, including a programmable gate array (PGA) such as a field programmable gate array (FPGA), or another type of circuit that includes discrete gate and/or transistor logic. A processor for a computer system 700 may be a central processing unit (CPU), a graphics processing unit (GPU), or both. Additionally, any processor described herein may include multiple processors, parallel processors, or both. Multiple processors may be included in, or coupled to, a single device or multiple devices.

A "processor" as used herein encompasses an electronic component which is able to execute a program or machine executable instruction. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each including a processor or processors. Many programs have instructions performed by multiple processors that may be within the same computing device or which may even be distributed across multiple computing devices.

Moreover, the computer system 700 may include a main memory 720 and a static memory 730, where memories may can communicate with each other via a bus 708. Memories described herein are tangible storage mediums that can store data and executable instructions and are non-transitory during the time instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A memory described herein is an article of manufacture and/or machine component. Memories described herein are computer-readable mediums from which data and executable instructions can be read by a computer. Memories as described herein may be random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. Memories may be volatile or non-volatile, secure and/or encrypted, unsecure and/or unencrypted.

"Memory" is an example of a computer-readable storage medium. Computer memory is any memory which is directly accessible to a processor. Examples of computer memory include, but are not limited to RAM memory, registers, and register files. References to "computer memory" or "memory" should be interpreted as possibly being multiple memories. The memory may for instance be multiple memories within the same computer system. The memory may also be multiple memories distributed amongst multiple computer systems or computing devices.

As shown, the computer system 700 may further include a video display unit 750, such as a liquid crystal display (LCD), an organic light emitting diode (OLED), a flat panel display, a solid-state display, or a cathode ray tube (CRT). Additionally, the computer system 700 may include an input device 760, such as a keyboard/virtual keyboard or touch-sensitive input screen or speech input with speech recognition, and a cursor control device 770, such as a mouse or touch-sensitive input screen or pad. The computer system 700 can also include a disk drive unit 780, a signal generation device 790, such as a speaker or remote control, and a network interface device 740.

In an embodiment, as depicted in FIG. 7, the disk drive unit 780 may include a computer-readable medium 782 in which one or more sets of instructions 784, e.g. software, can be embedded. Sets of instructions 784 can be read from the computer-readable medium 782. Further, the instructions 784, when executed by a processor, can be used to perform one or more of the methods and processes as described herein. In an embodiment, the instructions 784 may reside completely, or at least partially, within the main memory 720, the static memory 730, and/or within the processor 710 during execution by the computer system 700.

In an alternative embodiment, dedicated hardware implementations, such as application-specific integrated circuits (ASICs), programmable logic arrays and other hardware components, can be constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing can be constructed to implement one or more of the methods or functionalities as described herein, and a processor described herein may be used to support a virtual processing environment.

The present disclosure contemplates a computer-readable medium 782 that includes instructions 784 or receives and executes instructions 784 responsive to a propagated signal; so that a device connected to a network 701 can communicate voice, video or data over the network 701. Further, the instructions 784 may be transmitted or received over the network 701 via the network interface device 740.

The computer system 700 can be used by or in conjunction with the second medical imaging system 640 in order to monitoring physiology of a patient as described herein. The computer system 700 can receive, download, collect or otherwise obtain raw sensor data from an initial set of sensors used to initially monitor physiology of the patient. The computer system 700 can then implement processes described herein to identify the optimal (e g, minimal) arrangement of sensors to monitor the patient. The optimal arrangement of sensors is defined by the physiology of the patient as determined based on the raw sensor data from the initial set of sensors. The computer system 700 may be used to perform the process live as the initial set of sensors collects the raw sensor data, such as in a clinical setting. As an example, the computer system 700 may be implemented on a laptop or desktop used by a technician or medical professional.

In an embodiment, a controller described herein may include a combination of more or less than all of the elements of the computer system 700 shown in FIG. 7. For example, a controller may include the processor 710 and a main memory 720 and/or a static memory 730. The controller may fully or partially execute a process described herein. For example, a controller may be a implemented in a system that includes the base station 630 and the image analysis computer 620, or at least that implements the functionality attributed herein to the base station 630 and the image analysis computer 620. As such, the controller may execute a process that includes, for example, any or all of defining the mitral valve annulus and/or coaptation plane. This may be accomplished by setting the slice position and orientation in an image volume (e.g. TEE) in such a way that the slice is coplanar with the mitral valve annulus plane and moving it along its normal to the mitral valve coaptation plane. Furthermore, a point set derived from polygon mesh describing the mitral valve annulus and/or the plane of mitral valve coaptation may be used for plane computation.

In an embodiment, the estimated TSP zone may be overlaid onto real-time imagery such as TEE, X-ray, polygon mesh or a similar mechanism. This may be performed using interventional tools that operate based on software suites.

Embodiments of the present disclosure include methods to estimate the mitral valve annulus plane, the mitral valve leaflet coaptation and or mitral valve leaflet defect. This can be achieved directly by either slicing an image volume or polygon mesh and finding the mitral valve annulus plane and moving this plane along its normal to the mitral valve leaflet coaptation or defect resulting in a normal vector (N) describing the plane orientation and a point (P) describing the location of the mitral valve leaflet coaptation or defect. Furthermore, a point set laying coplanar on the mitral valve annulus plane and a point (set) describing the mitral valve leaflet coaptation or defect derived from polygon meshes or any other form can be used to compute mitral valve annulus/coaptation plane. A principal component analysis applied to the mitral valve annulus point set may be used to estimate the vectors of the main variation in the data. The vector with the least variation (smallest eigenvalues) will be parallel with the normal of the mitral valve annulus plane. This normal vector and the mitral valve coaptation or defect then give the plane of coaptation.

Embodiments of the present disclosure include methods of visualizing and/or displaying the optimal puncture site/region onto the intra-atrial septum. This may be accomplished by combining a predefined puncture height with the mitral valve plane normal and projecting this point onto the intra-atrial septum of a polygon mesh along the axis 102 of the mitral valve. These metrics and safety ranges can also be derived from the delivery apparatus, based on patient anatomy and/or based on additional or alternative factors including others described elsewhere herein. Additionally, a TSP may not always be possible at the indicated location due to anatomical and device constrains. Therefore, a safe puncture region may be shown with sufficient height above the mitral valve instead of a single point. As described herein, such a zone is described as a safe zone, and may be generated and displayed based on predetermined criteria and dynamic analysis of patient physiology. An optimal TSP may be accomplished when puncturing in the region between the planes defining the safe zone.

In another embodiment such as in FIG. 4B, an ellipsoid shaped "heat" map centered on the optimal TSP point may be displayed to indicate any punctures that are off the mitral valve-axis. Additionally, polygon meshes modelling the heart chambers may be used to visualize the optimal puncture zone.

The teachings of the present disclosure address the problems described in the background. Accordingly, trans-septal puncture guidance for heart repair enables optimal guidance for a puncture performed via TSP, which in turn may increase safety and provide better results in providing remedies for damaged and/or malfunctioning mitral valves.

Although trans-septal puncture guidance for heart repair has been described with reference to several exemplary embodiments, it is understood that the words that have been used are words of description and illustration, rather than words of limitation. Changes may be made within the purview of the appended claims, as presently stated and as amended, without departing from the scope and spirit of trans-septal puncture guidance for heart repair in its aspects. Although trans-septal puncture guidance for heart repair has been described with reference to particular means, materials and embodiments, trans-septal puncture guidance for heart repair is not intended to be limited to the particulars disclosed; rather trans-septal puncture guidance for heart repair extends to all functionally equivalent structures, methods, and uses such as are within the scope of the appended claims.

For example, the teaching described herein mainly relate to the relationship between a TSP and mitral valve repairs. However, inasmuch as TSP may be performed for other purposes now or in the future, teachings described herein may be adopted as the basis for identifying an optimal TSP location or safe zone even for repairs away from the mitral valve. Similarly, the teachings described herein may be leveraged to identify safe zones for optimizing other types of punctures outside of an intra-atrial septum using medical imaging modes identical to or similar to those described herein.

The illustrations of the representative embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A controller for providing puncture site guidance during a heart repair procedure, the controller comprising:
   a memory that stores instructions, and
   a processor that executes the instructions, wherein when executed by the processor, the instructions cause the controller to:
   receive image data of a heart of a patient during the heart repair procedure, wherein the heart comprises a mitral valve and an intra-atrial septum, and the mitral valve comprises a mitral valve annulus;
   define a mitral valve annulus plane along the mitral valve annulus and a normal vector perpendicular to the mitral valve annulus plane;
   define an offset plane that intersects with the intra-atrial septum, wherein the offset plane is parallel to the mitral valve annulus plane and is located at a distance that is offset from the mitral valve annulus plane by an offset amount;
   display imagery of the heart based on the image data;
   define a safe zone to puncture the intra-atrial septum based on location of the mitral valve, wherein the safe zone is defined by generation of (i) a lower boundary plane that is parallel to the offset plane and located below the offset plane by a first specified distance and (ii) an upper boundary plane that is parallel to the offset plane and located above the offset plane by a second specified distance; and
   display the safe zone on the intra-atrial septum in the displayed imagery of the heart.

2. The controller of claim 1, wherein, when executed by the processor, the instructions further cause the controller to:
   identify a long axis of the mitral valve, the long axis having an axial direction,
   identify a long axis plane that intersects with the offset plane and that passes through the long axis and is parallel to the normal vector, and
   identify and display an optimal puncture site point on the intra-atrial septum at an intersection of the long axis plane and the offset plane.

3. The controller of claim 1, wherein the offset amount is predetermined.

4. The controller of claim 1, wherein, when executed by the processor, the instructions further cause the controller to:
   determine and display an optimal puncture site point on the intra-atrial septum within the safe zone based on the offset plane.

5. The controller of claim 1, wherein, when executed by the processor, the instructions further cause the controller to:
   determine the first specified distance and the second specified distance to define levels between which puncture of the intra-atrial septum is determined to be safe.

6. The controller of claim 1, wherein, when executed by the processor, the instructions further cause the controller to:
   define a three-dimensional coordinate system for the image data of the heart, and
   define each of the mitral valve annulus plane, the normal vector, the offset plane, the lower boundary plane, and the upper boundary plane in the three-dimensional coordinate system.

7. The controller of claim 1, wherein, when executed by the processor, the instructions further cause the controller to:
   dynamically generate at least one of the offset amount, the first specified distance, and the second specified distance.

8. The controller of claim 1, wherein, when executed by the processor, the instructions further cause the controller to:
   co-register live image data of the heart that is captured live during the heart repair procedure with previous three-dimensional image data of the heart captured previously to generate the image data.

9. The controller of claim 8, wherein the live image data comprises three-dimensional image data captured by ultrasound imaging.

10. The controller of claim 1, wherein the distance comprises a height between and perpendicular to the mitral valve annulus plane and the offset plane.

11. A method for providing optimal puncture site guidance during a heart repair procedure, the method comprising:
   receiving image data of a heart of a patient during the heart repair procedure, wherein the heart comprises a malfunctioning part and a barrier through which an access point is to be identified to access the malfunctioning part, and the malfunctioning part comprises a measurable part through or along which a measurable plane passes that can be measured;

defining the measurable plane through or along the measurable part of the malfunctioning part, the measurable plane having a normal vector;

defining an offset plane that intersects with the barrier, wherein the offset plane is parallel to the measurable plane and is located at a distance that is offset from the measurable plane by an offset amount;

displaying imagery of the heart on a display based on the image data;

defining a safe zone to puncture the barrier based on location of the mitral valve, wherein the safe zone is defined by generation of (i) a lower boundary plane that is parallel to the offset plane and located below the offset plane by a first specified distance and (ii) an upper boundary plane that is parallel to the offset plane and located above the offset plane by a second specified distance;

defining an optimal puncture site point on the barrier within the safe zone to punction the barrier during the heart repair procedure; and displaying the safe zone and the optimal punction site point on the barrier in the displayed imagery of the heart.

12. The method for displaying an optimal puncture site of claim 11, further comprising:

identifying a long axis of the malfunctioning part, the long axis having an axial direction, identifying a long axis plane that intersects with the offset plane and that passes through the long axis and is parallel to the normal vector, and displaying the optimal puncture site point on the barrier at an intersection of the long axis plane and the offset plane.

13. The method of claim 11, wherein the imagery of the heart is displayed with the optimal puncture site point, the lower boundary plane, and the upper boundary plane in real-time during a medical intervention.

14. A system for providing puncture site guidance during a heart repair procedure, the system comprising:

a controller that includes a memory that stores instructions, and a processor that executes the instructions;

a medical imaging system configured to generate image data for images of a heart of a patient, wherein the heart comprises a mitral valve and an intra-atrial septum, and the mitral valve comprises a mitral valve annulus; and a display controlled by the controller, the display configured to display images of the heart based on the image data, wherein when executed by the processor, the instructions cause the controller to:

receive the image data of the heart of a patient during the heart repair procedure from the medical imaging system;

define a mitral valve annulus plane along the mitral valve annulus and a normal vector perpendicular to the mitral valve annulus plane;

define an offset plane that intersects with the intra-atrial septum, wherein the offset plane is parallel to the mitral valve annulus plane and is located at a distance that is offset from the mitral valve annulus plane by an offset amount;

display, on the display, the images of the heart;

define a safe zone to puncture the intra-atrial septum based on location of the mitral valve, wherein the safe zone is defined by generation of (i) a lower boundary plane that is parallel to the offset plane and located below the offset plane by a first specified distance and (ii) an upper boundary plane that is parallel to the offset plane and located above the offset plane by a second specified distance; and display the safe zone on the intra-atrial septum in the displayed imagery of the heart.

15. The system of claim 14, wherein the medical imaging system is configured to generate image data of the heart in three dimensions.

16. The controller of claim 1, further comprising:

an arrangement of sensors configured to measure the physiology of the patient and generate patient physiology data; and wherein, when executed by the processor, the instructions further cause the controller to:

dynamically generate at least one of the offset amount, the first specified distance, and the second specified distance based on dynamic analysis of the patient physiology data.

17. The controller of claim 1, wherein, when executed by the processor, the instructions further cause the controller to:

dynamically generate at least one of the offset amount, the first specified distance, and the second specified distance based on at least one of (a) physiology of the patient measured during the heart repair procedure and (b) one or more selected devices used during the heart repair procedure.

18. The method of claim 11, further comprising:

dynamically generate at least one of the offset amount, the safe distance below the offset plane, and the safe distance above the offset plane based on dynamic analysis of patient physiology data generated by an arrangement of sensors configured to measure the physiology of the patient.

19. The system of claim 14, further comprising:

an arrangement of sensors configured to measure the physiology of the patient and generate patient physiology data; and wherein, when executed by the processor, the instructions further cause the controller to:

dynamically generate at least one of the offset amount, the first specified distance, and the second specified distance based on dynamic analysis of the patient physiology data.

20. The system of claim 14, wherein, when executed by the processor, the instructions further cause the controller to:

dynamically generate at least one of the offset amount, the first specified distance, and the second specified distance based on at least one of (a) physiology of the patient measured during the heart repair procedure and (b) one or more selected devices used during the heart repair procedure.

* * * * *